United States Patent [19]
Alam et al.

[11] Patent Number: 5,997,884
[45] Date of Patent: Dec. 7, 1999

[54] COMPOSITIONS AND METHOD FOR TREATING MIGRAINE

[75] Inventors: Abu Alam, Lake Forest; Pablo J. Diaz Cruz, Decatur; Keith Glad, Springfield; Dennis Roberts, Decatur, all of Ill.

[73] Assignee: Taylor Pharmaceuticals, Buffalo Grove, Ill.

[21] Appl. No.: 09/022,436

[22] Filed: Feb. 12, 1998

[51] Int. Cl.$^6$ ............................... A61K 9/00; A61K 9/08
[52] U.S. Cl. ............................ 424/400; 514/338; 514/339
[58] Field of Search ..................................... 424/422, 400; 514/338, 339

[56] References Cited

U.S. PATENT DOCUMENTS

| | | |
|---|---|---|
| 3,966,748 | 6/1976 | Hofmann et al. . |
| 5,266,580 | 11/1993 | Chiou . |
| 5,288,497 | 2/1994 | Stanley et al. . |
| 5,310,561 | 5/1994 | Jao et al. . |

OTHER PUBLICATIONS

Anderson Price et al, Pathophysiology, Clinical Concepts of Disease Processes, 3rd ed., p. 82, 1986.

Nageotte et al., American Journal of Obstetrics and Gynecology, Droperidol and Diphenhydramine in the Management of Hyperemsis gravidarum, 174/6 (1801–6) (abstract), 1996.

Kymer et al., Journal of Clinical Anesthesia, The Effects of Oral Droperidol Versus Oral Metoclopramide . . . When Used as a Premedicant for Strabismus Surgery, 7/1 (35–9), Feb. 1995.

Wang, et al. *Droperidol Treatment of Status Migrainosus and Refractory Migraine*, Headache. Jun., 1997, pp. 377–382.

Wang, et al. *Droperidol Treatment of Acute Refractory Migraine and Status Migrainosus*, Headache, Apr., 1996, p. 280.

John F. Rothrock, MD., *Treatment of Acute Migraine with Intravenous Droperidol*, Headache, Apr. 1997, pp. 256–257.

*Primary Examiner*—Thurman K. Page
*Assistant Examiner*—Brian K. Seidleck
*Attorney, Agent, or Firm*—Leydig, Voit & Mayer, Ltd.

[57] ABSTRACT

An aqueous solution of droperidol suitable for injection having a concentration from about 0.1 to about 10.0 mg/ml, and a sufficient amount of tonicity adjusting agent to render the solution isotonic, the solution being in a sealed container. Also provided is an aqueous solution of droperidol suitable for injection, comprising droperidol at a concentration from about 2.75 to about 10 mg/ml, and the solution being in a sealed container.

8 Claims, No Drawings

COMPOSITIONS AND METHOD FOR TREATING MIGRAINE

FIELD OF THE INVENTION

This invention relates to the field of migraine treatment.

BACKGROUND OF THE INVENTION

The prevalence of migraine is said to be approximately 6% of the male population and 18% of the female population. Treatment for many patients having the occasional migraine usually involves simple analgesics, non-steroidal anti-inflammatory agents, or specific agents such as ergotamines or triptans. Approximately 10% of migraine sufferers have three or more attacks per month and warrant prophylactic treatment. Preventative agents such as beta-blockers, tricyclic antidepressants and divalproex sodium can reduce but not eliminate migraine attacks in some patients. Thus, there remains a need for migraine specific medications such as sumatriptan. In the remaining population of migraine sufferers, and in those with intolerable side-effects from available drugs, there is a lack of conventional pharmaceutical preparations that exhibit therapeutic effect, without severe side-effects.

Droperidol presently is marketed by Akorn, Inc. under the trademark Inapsine, as an injectable formulation used in anesthesia for preoperative surgery. It has never been approved for use in the treatment or management of migraine attacks. The concentration of droperidol in the Inapsine is 2.5 mg/ml. That is the only concentration of droperidol that has been approved for human injection. Further, droperidol is present as the lactate salt in Inapsine. No droperidol salt, other than the lactate, has been used for human injection.

A limited, uncontrolled, non-blinded, use of droperidol lactate (2.5 mg/ml droperidol) to treat migraine attacks was attempted and the results published in *Headache*, April 1996, p.280. In that publication it was reported that 20 patients received from 2.5 to 7.5 mg droperidol intravenously, in increments of 2.5 mg every 30 minutes until the patient was headache free or until a total of three doses had been administered. All of the patients received prior treatment with migraine therapies. Eighteen of the patients reported to be headache-free by the last dose. Although the article reports on apparently encouraging results in treating migraine attacks with droperidol, no definitive conclusions can be reached from the results reported in that article as the number of patients treated was small, the study was not blinded, all patients received other agents to treat the migraine episode prior to receiving droperidol, and there was no placebo control. Also, there was no attempt to repeat the results with the patients. Further, no attempt was made to prolong therapy beyond the initial treatment to a headache-free state and most patients had continuing symptoms to some degree within 24 hours after the last droperidol treatment.

The study used multiple treatments of droperidol, with many patients receiving more than 2.5 mg of droperidol to reduce the migraine symptoms. The problem with administering droperidol at such a concentration is that the patient receives a significant volume of fluid in order to achieve a therapeutically effective amount of droperidol. This is of particular concern if the patient is receiving the droperidol through intramuscularly (I.M.) injection. Muscle pain and irritation and other problems may be associated with such large fluid injections.

SUMMARY OF THE INVENTION

In accordance with the present invention, droperidol is supplied in a dosage form that provides better patient tolerance and improved ease of administration.

The dosage forms provide a higher concentration of droperidol than has been available previously. In particular, the dosage forms contain from 2.75 to 10.0 mg/ml of droperidol.

The dosage forms of the present invention may be used to treat migraine episodes, by administration, either intravenously ("I.V.") or intramuscularly ("I.M."), to a patient during a migraine attack, in an amount that is effective to treat symptoms of migraine. The dosage forms of droperidol may be used without pretreatment or in conjunction with other migraine therapies.

The dosage forms of the present invention also may be used to treat patients that are suffering from tension headache, vertigo, or hyperemesis gravidarum. The dosage forms also may be used as antiemetics, to treat nausea and the like, such as that caused by chemotherapy. In each instance the dosage is administered in an amount sufficient to treat the patient's symptoms.

The present invention also provides a dosage form of droperidol that is more suitable for injection, as by having a tonicity adjusting agent present to render the formulation isotonic. Such a dosage form may have from 0.1 to 10mg/ml of droperidol. Such a dosage form may also be pH adjusted to be of a physiologic pH.

DETAILED DESCRIPTION OF THE PREFERRED EMBODIMENTS

As indicated, the present invention provides dosage forms of droperidol at concentrations from 0.1, 2.75, 5.5, 8.25 and 10.0 mg/ml droperidol that are particularly useful.

The droperidol may be present as the lactate, or other suitable organic salts of droperidol may be used, such as tartrate or acetate. The salt is usually formed in situ by the addition of a suitable organic acid, such as lactic acid, tartaric acid, acetic acid, or the like. The amount of acid that is added is usually sufficient to adjust the solution to a pH from about 3 to about 5.

The dosage forms of the present invention may be rendered isotonic, to increase patient tolerance. Accordingly, the solutions may be rendered isotonic by use of a suitable tonicity adjusting agent, such as glycerin. Accordingly, a sufficient amount of a tonicity adjusting agent may be present to render the solution isotonic, or nearly so.

After the solution is formed, it should be sterilized, as by filtration, or any other suitable means. Alternatively, the solution may be terminally sterilized by autoclaving after filling into containers.

The dosage forms of the present invention include solutions contained in ampules, vials, prefilled syringes, and the like. Also, multi-dose vials may be used. In such an instance it is desirable to have a preservative present in the solution, such as a paraben, usually methyl and/or propyl paraben. Preservatives, of course, may be present in any of the dosage forms of the present invention.

As indicated, patients that are suffering from a migraine episode, tension headache, vertigo, hyperemesis gravidarum, or nausea. The patients are administered the droperidol, via either I.V. or I.M. The droperidol is typically administered in dosages of 2.75 to 10.0 mg until the symptoms subside. The maximum dosage of droperidol administered to a patient at a single session usually will be 7.5 mg, although it may on occasion be as high as 10 mg.

The patients receiving droperidol to treat migraine may be treated with droperidol as a single therapy. By this it is meant that other agents used to treat an active episode of migraine need not be used prior to or in conjunction with the droperidol treatment. Many patients receive various medications for prophylaxis against active migraine episodes, but such prophylactic therapy is not considered to be pretreatment of an active migraine episode, prior to droperidol treatment. Such therapy is nonspecific in that the goal is to prevent or reduce the number of occurrences of active migraine headache, but not the treatment of a specific migraine episode. The present dosage forms will be useful as a first-line treatment of active migraine headache without the prior use of traditional migraine therapy, or as a rescue medication when other treatment has failed.

Presently, an active migraine episode may be treated with any of a number of therapies, including the following: Simple analgesics, such as aspirin, combination analgesics as with caffeine, vasoconstrictors, narcotics, and the like.

As indicated, the use of droperidol in accordance with the present invention does not require the prior administration of such other agents for treating migraine.

The migraine patients to whom droperidol should be administered are those that are experiencing a migraine episode or are at risk of such an episode. Such patients may be generally described as those meeting the diagnostic criteria for "migraine with aura" or "migraine without aura" as detailed in: "Classification Committee of the International Headache Society. Classification and Diagnostic Criteria For Headache Disorders, Cranial Neuralgia and Facial Pain", Cephalgia, 1988, Vol. 8, Supp. 77 at pp. 19–21; or meeting the diagnostic criteria for "status migrainosus", as detailed therein at pp. 26–27.

The droperidol of use in accordance with the present invention may be administered either I.V. or I.M. If administered intravenously, the rate of infusion is not critical and will usually be administered by I.V. push in a pre-established line. Usually the droperidol will be administered intramuscularly as a bolus.

For some patients it may be beneficial to administer an additional dose of droperidol after the headache has subsided to reduce the probability that the headache will return in a short period of time. Such an additional dose of droperidol may be used to avoid the use of sedative or other analgesics within the next few hours after the headache symptoms have subsided. Presently it is typical for patients, after they have been rendered headache-free, to resort to such remedies as sedation or use of analgesics shortly after the headache symptoms have subsided to reduce the recurrence of the migraine symptoms after the patient has become headache-free. The present invention may avoid the need for such remedies.

EXAMPLES

In accordance with the present invention, droperidol lactate solutions were prepared having concentrations of 0.1, 2.75, 5.5, 8.25 and 10.0 mg droperidol per ml. Lactic acid was added to water-for-injection, which was then heated to 65° C. The droperidol was then added and mixed until dissolved. The droperidol was filled into syringes (1 cc/1.5 cc syringe). These dosage forms were terminally sterilized and placed on stability. The results of the stability study at 25° and 40° C. are shown in Table I.

In a similar fashion, a solution of droperidol lactate was prepared (10 mg/ml) using glycerin to render the solutions isotonic, filled into syringes (1 cc/1.5cc syringe), terminally sterilized, and placed on stability. The results of the stability study at 25° C. and 40° C. are shown in Table II. Additionally, a solution of droperidol tartrate was prepared (using tartaric acid in place of lactic acid) and similarly filled, sterilized and placed on stability. The results of the stability study at 25° and 40° C. are shown in Table III. Further, a solution of droperidol lactate preserved with methyl and propyl paraben was prepared, filled, sterilized and placed on stability. The results of the stability study at 25° C. and 40° C. are shown in Table IV.

TABLE I

Droperidol stability from various formulations of the lactate salt packaged in a syringe on accelerated storage at 40° C. and room temperature at 25° C.

| Analysis | 0.1 mg/ml | 2.75 mg/ml | 5.5 mg/ml | 8.25 mg/ml | 10 mg/ml |
| --- | --- | --- | --- | --- | --- |
| Initial values: | | | | | |
| Appearance | clear | clear | clear | clear | clear |
| pH | 3.8 | 3.3 | 3.3 | 3.3 | 3.1 |
| Assay, % | 99.2 | 99.7 | 100.0 | 100.6 | 100.5 |
| Osmolality | 56 | 106 | 162 | 106 | 116 |
| 40° C./4 wks | | | | | |
| Appearance | clear | clear | clear | clear | clear |
| pH | 4.0 | 3.4 | 3.3 | 3.3 | 3.2 |
| Assay, % | 99.7 | 98.4 | 97.3 | 99.4 | N.D. |
| Osmolality | 3 | 41 | 79 | 113 | 134 |
| 40° C./8 wks | | | | | |
| Appearance | clear | clear | clear | clear | clear |
| pH | 3.8 | 3.3 | 3.3 | 3.3 | 3.2 |
| Assay, % | 99.7 | 100.7 | 100.7 | 100.8 | 99.0 |
| Osmolality | 3 | 39 | 77 | 110 | 135 |
| 25° C./4 wks | | | | | |
| Appearance | clear | clear | clear | clear | clear |
| pH | 3.8 | 3.3 | 3.3 | 3.3 | 3.2 |
| Assay, % | 99.1 | 99.5 | 97.0 | 100.1 | N.D. |
| Osmolality | 3 | 41 | 76 | 115 | 131 |

TABLE I-continued

Droperidol stability from various formulations of the lactate salt packaged in a syringe on accelerated storage at 40° C. and room temperature at 25° C.

| Analysis | 0.1 mg/ml | 2.75 mg/ml | 5.5 mg/ml | 8.25 mg/ml | 10 mg/ml |
|---|---|---|---|---|---|
| 25° C./8 wks | | | | | |
| Appearance | clear | clear | clear | clear | clear |
| pH | 3.8 | 3.3 | 3.3 | 3.3 | 3.2 |
| Assay, % | 100.1 | 100.6 | 100.3 | 99.6 | 98.7 |
| Osmolality | 2 | 39 | 74 | 111 | 129 |

N.D.—not done

TABLE II

Stability of droperidol 10 mg/ml formulation using lactate salt and glycerin to adjust tonicity

| Analysis | Initial | 40° C./ 4 wks | 40° C./ 8 wks | 25° C./ 4 wks | 25° C./ 8 wks |
|---|---|---|---|---|---|
| Appearance | clear | clear | clear | clear | clear |
| pH | 3.1 | 3.2 | 3.2 | 3.1 | 3.2 |
| Assay, % | 99.7 | N.D. | 98.4 | N.D. | 98.1 |
| Osmolality | 309 | 333 | 322 | 328 | 315 |

N.D.—not done

TABLE III

Stability of droperidol 10 mg/ml formulation using tartrate salt

| Analysis | Initial | 40° C./ 4 wks | 40° C./ 8 wks | 25° C./ 4 wks | 25° C./ 8 wks |
|---|---|---|---|---|---|
| Appearance | clear | clear | clear | clear | clear |
| pH | 3.5 | 3.5 | 3.5 | 3.5 | 3.5 |
| Assay % | 101.1 | N.D. | 99.7 | N.D. | 99.7 |
| Osmolality | 44 | 44 | 44 | 44 | 44 |

N.D.—not done

TABLE IV

Stability of droperidol 10 mg/ml formulation using lactate salt and preserved with methyl paraben and propyl paraben

| Analysis | Initial | 40° C./ 4 wks | 40° C./ 8 wks | 25° C./ 4 wks | 25° C./ 8 wks |
|---|---|---|---|---|---|
| Appearance | clear | clear | clear | clear | clear |
| pH | 3.1 | 3.2 | 3.1 | 3.1 | 3.1 |
| Assay, % | 101.1 | N.D. | 99.5 | N.D. | 98.7 |
| Osmolality | 150 | 162 | 159 | 154 | 153 |
| Methyl paraben, mg/ml | 1.64 | N.D. | 1.71 | N.D. | 1.77 |
| Propyl paraben, mg/ml | 0.18 | N.D. | 0.17 | N.D. | 0.17 |

N.D.—not done

What is claimed is:

1. A method of treating a patient suffering from a migraine episode or tension headache, comprising administering droperidol, either intravenously or intramuscularly, to the patient, in an amount that is effective to treat said symptoms, wherein said droperidol is an aqueous solution having a concentration from about 2.75 to about 10.0 mg/ml.

2. The method of claim 1 wherein the patient is suffering from a migraine episode.

3. The method of claim 1 wherein the aqueous solution further comprises a tonicity adjusting agent.

4. The method of claim 3 wherein the tonicity adjusting agent is glycerin.

5. The method of claim 3 wherein the aqueous solution further comprises a preservative.

6. The method of claim 1 wherein the droperidol is present as a lactate salt.

7. The method of claim 1 wherein the droperidol is present as a tartrate salt.

8. The method of claim 1 wherein the droperidol is present as an acetate salt.

* * * * *